United States Patent [19]

Archibald et al.

[11] Patent Number: 5,068,337

[45] Date of Patent: Nov. 26, 1991

[54] 1,4-DIHYDROPYRIDINES AND THEIR ABILITY TO INHIBIT BLOOD PLATELET AGGREGATION, INHIBIT THROMBOXANE SYNTHETASE AND PHOSPHOLIPASE

[75] Inventors: John L. Archibald, Farnham Royal; Terence J. Ward; Albert Opalko, both of Maidenhead, all of England

[73] Assignee: John Wyeth & Brother Limited, Maidenhead, Great Britain

[21] Appl. No.: 930,972

[22] Filed: Nov. 13, 1986

Related U.S. Application Data

[63] Continuation of Ser. No. 760,707, Jul. 30, 1985, abandoned.

[30] Foreign Application Priority Data

Aug. 17, 1984 [GB] United Kingdom .................. 8421039
Jun. 21, 1985 [GB] United Kingdom .................. 8515751

[51] Int. Cl.$^5$ .................. A61K 31/505; C07D 401/04; C07D 471/04
[52] U.S. Cl. ............................. 514/256; 544/333; 514/307; 514/308; 514/311; 514/312; 514/314; 514/339; 514/341; 514/342; 514/343; 514/350; 514/356; 546/118; 546/121; 546/141; 546/143; 546/144; 546/147; 546/148; 546/153; 546/157; 546/167; 546/256; 546/257; 546/271; 546/263; 546/279; 546/280; 546/281; 546/283; 546/284; 546/298; 546/321
[58] Field of Search ............... 546/263, 278, 280, 281, 546/271, 141, 143, 147, 153, 332, 341, 342, 343, 338, 118, 162, 167, 157, 307, 308, 310, 313, 312, 311, 303; 544/333; 514/256, 314, 350, 356, 314

[56] References Cited

U.S. PATENT DOCUMENTS 4,492,703  1/1985  Goldmann et al. .................. 546/321

FOREIGN PATENT DOCUMENTS 88274   9/1983  European Pat. Off. .
100189  2/1984  European Pat. Off. .
2738153 3/1979  Fed. Rep. of Germany .
2844595 4/1980  Fed. Rep. of Germany .
8047656 4/1980  Japan .
1552911 9/1979  United Kingdom .
2034693 6/1980  United Kingdom .
1585978 3/1981  United Kingdom .

OTHER PUBLICATIONS

Chem. Abs. 94:15570a (1981) and Der. Abs. 80-35660C/20 of Jpn Kukai 8047656.

*Primary Examiner*—Alan L. Rotman
*Attorney, Agent, or Firm*—Arthur G. Seifer

[57] ABSTRACT

The invention concenrs compounds of formula

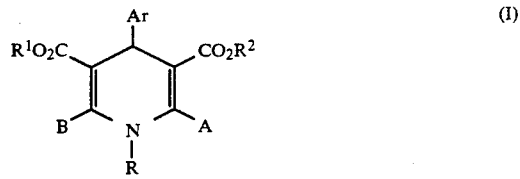

or salts thereof; wherein
Ar is an optionally substituted aryl radical;
R represents hydrogen or an optionally substituted alky or aralkyl group;
$R^1$ and $R^2$ are the same or different and are selected from hydrogen and saturated or unsaturated, cyclic or acyclic aliphatic hydrocarbon residues optionally substituted by one or more groups selected from halogen, OH, carboxy, CN, alkoxy, alkylthio, aryloxy, alkoxycarbonyl, amino, substituted amino, and optionally substituted aryl;
A represents a group of formula $-XR^3$ wherein X is (i) a group of formula $-(CHR^6)_p-Y-(CHR^7)_q-$ or (ii) a group of formula $-(CHR^6)_r-O-(CHR^7)_s$ in which formulae: Y represnets $-S-$, $NR^8$ or a direct bond, p and q each represent 0, 1 or 2 providing that p and q do not both represents 0, 1 or 2 and the other is zero; $R^6$, $R^7$ and $R^8$ independently represent hydrogen or lower alkyl, and $R^3$ is an optionally substituted nitrogen ring heteroaryl radical optionally containing other ring heteroatoms selected from oxygen, nitrogen or sulphur; B represents hydrogen, carboxyl, lower alkoxycarbonyl, lower alkyl optionally substituted by amino, lower alkoxy, lowr alkoxycarbonyl or carboxyl, or amino optionally substituted by one or two lower alkyl groups, which compounds possess anithypertensive and antithromotic activity.

25 Claims, No Drawings

1,4-DIHYDROPYRIDINES AND THEIR ABILITY TO INHIBIT BLOOD PLATELET AGGREGATION, INHIBIT THROMBOXANE SYNTHETASE AND PHOSPHOLIPASE

This application is a continuation, of application Ser. No. 760,707, filed July 30, 1985.

This invention relates to heterocyclic compounds possessing pharmaceutical activity, more particularly to 1,4-dihydropyridine, processes for preparing them and pharmaceutical compositions containing them.

In one aspect this invention provides a compound of formula

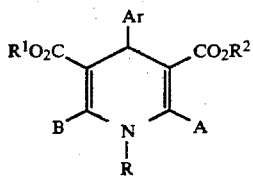

or a salt thereof; wherein:
Ar is an optionally substituted aryl radical;
Ar represents hydrogen or an optionally substituted alkyl or aralkyl group;
$R^1$ and $R^2$ are the same or different and are selected from hydrogen and saturated or unsaturated, cyclic or acyclic aliphatic hydrocarbon residues optionally substituted by one or more groups selected from halogen, OH, carboxy, CN, alkoxy, alkylthio, aryloxy, alkoxycarbonyl, amino, substituted amino, and optionally substituted aryl;
A represents a group of formula $-XR^3$ wherein
X is (i) a group of formula $-(CHR^6)_p-Y-(CHR^7)_q-$ or (ii) a group of formula $-(CHR^6)_r-O-(CHR^7)_s-$
in which formulae: Y represents $-S-$, $NR^8$ or a direct bond, p and q each represent 0, 1 or 2 providing that p and q do not both represent zero when Y is a direct bond; one of r and s represents 0, 1 or 2 and the other is zero; $R^6$, $R^7$ and $R^8$ independently represent hydrogen or lower alkyl, and $R^3$ is an optionally substituted nitrogen ring heteroaryl radical optionally containing other ring heteroatoms selected from oxygen, nitrogen or sulphur B represents hydrogen, carboxyl, lower alkoxycarbonyl, lower alkyl optionally substituted by lower alkoxy, lower alkoxycarbonyl, carboxy or amino, or amino optionally substituted by one or two lower alkyl groups.

By the term aryl when used as a group or part of a group (e.g. aryloxy, arylalkyl) is meant any monovalent carbocyclic or heterocyclic radical possessing aromatic character and includes groups having 5 to 10 ring atoms such as phenyl, naphthyl, pyridyl (e.g. 2-, 3-or 4-pyridyl), thienyl (e.g. 2-thienyl) furyl (e.g. 2-furyl), quinolyl (e.g. 2-, 3- or 4-quinolyl), isoquinolyl (e.g. 2,3- or 4-isoquinolyl) and benzimidazolyl. Preferred heteroatoms are nitrogen, oxygen and sulphur. Examples of heterocyclic aromatic rings containing two heteroatoms are imidazolyl, e.g. 1-imidazolyl, thiazolyl e.g. 2-thiazolyl and pyrimidyl e.g. 2-pyrimidyl.

The term alkyl when used to signify a group or part of a group such as arylalkyl or alkyloxy means any straight or branched saturated aliphatic hydrocarbon especially those having 1 to 6 carbon atoms, e.g. 1-4 carbon atoms, or cyclic saturated aliphatic hydrocarbons especially those of 5 to 7 carbon atoms. Examples are methyl, ethyl, n-propyl, isopropyl, n-butyl, n-hexyl and cyclohexyl.

By the term optionally substituted' is meant optional substitution on carbon atoms by one or more substituents, e.g. substituents commonly used in pharmaceutical chemistry, e.g. halogen (e.g. Cl,Br, F), alkyl, alkyloxy, haloalkyl (e.g. $CF_3$), or haloalkoxy (e.g. $CHF_2O-$, $CF_3CH_2O-$), $NO_2$, $NH_2$, CN, alkylamino, dialkylamino, carboxy, alkyloxycarbonyl, acyl, acylamino, aryl (e.g. phenyl) or aminoalkyl.

Examples of the group R are groups as described above in connection with alkyl, aryl and arylalkyl and include hydrogen, methyl, ethyl, n-propyl, isopropyl and benzyl. Preferably R is hydrogen.

The groups $R^1$ and $R^2$ can be independently hydrogen, or saturated or unsaturated acyclic hydrocarbon chains of 1 to 6 carbon atoms, e.g. lower alkyl or alkenyl, optionally substituted by aryl of 5 to 10 ring atoms, lower alkoxy, amino, diloweralkylamino, carboxyl or lower alkoxycarbonyl.

Examples of $R^1$ and/or $R^2$ are methyl, ethyl, n-propyl, isopropyl, butyl, methoxymethyl, methoxyethyl, ethoxymethyl, ethoxyethyl, methoxypropyl, aminomethyl, 2-aminoethyl, 3-aminopropyl, dimethylaminoethyl, 2-carboxyethyl, ethoxycarbonylmethyl. When $R^1$ or $R^2$ is alkyl substituted by optionally substituted aryl (including heteroaryl) examples are benzyl, pyridylmethyl or -ethyl (e.g. 3-pyridylmethyl), imidazolylmethyl (e.g. 1-imidazolylmethyl) or imidazoylethyl.

Preferred values for $R^1$ and/or $R^2$ are methyl and ethyl.

Examples of $R^3$ are imidazolyl (e.g. 1 or 3-imidazolyl), pyridyl (e.g. 2 or 3-pyridyl), thiazolyl (e.g. 2-thiazolyl), pyrrolyl (e.g. 1-pyrrolyl) or bicyclic rings such as benzimidazolyl (e.g. 1-benzimidazolyl), quinolyl (e.g. 2-or 4-quinolyl), isoquinolyl (e.g. 1- or 4-isoquinolyl), imidazopyridyl (e.g. 5-imidazo[1,5-a]-pyridyl). Preferred values are 1-imidazolyl, 3-pyridyl and 5-imidazo[1,5-a]-pyridyl.

Examples of X are independently $-NH$; $-O-$; $-S-$; $-CH_2-$; $-CH(CH_3)-$; $-OCH_2-$; $-CH_2O$; $-(CH_2)_2-O-$; $-CH_2CH(CH_3)-$; $CH(CH_3)CH_2-$; groups of formula $-CH_2-Z-CH_2-$, $-CH_2-Z-(CH_2)_2-$, $-(CH_2)_2-Z-CH_2-$ where Z is S, NH or a direct bond.

Examples of B are $H-$, $CH_3-$, $NH_2-$, $NMe_2-$, $NHMe-$, $NH_2CH_2-$, $CH_3CH_2-$, $CH_{30}CH_2-$, $CH_{3OO}C-$, $HOOC-$, $CH_3OOCCH_2-$ and $HOOCCH_2-$. Preferred examples of B are $CH_3-$ and $NH_2$.

Preferred examples of X are $-CH_2-$, $-(CH_2)_2-$, $-CH(CH_3)-$, $-CH_2CH(CH_3)-$, $-CH(CH_3)CH_2-$, $-CH_2O-$, $-CH_2NH-$ and $-CH_2-S-$.

Examples of Ar are groups mentioned above for the definitions of aryl and included in the preferred values are 2- and/or 3-substituted phenyl groups, e.g. 2-and/or 3-nitrophenyl; 2,3-dichlorophenyl; 2-trifluoromethylphenyl, pentafluorophenyl, naphthyl (e.g. 1-naphthyl), pyridyl (e.g. 2-pyridyl), halopyridyl (e.g. 2-chloropyrid-3-yl), benzimidazolyl (e.g. 4- or 7-benzimidazolyl.

Particularly preferred compounds provided by this invention have formula Ia:

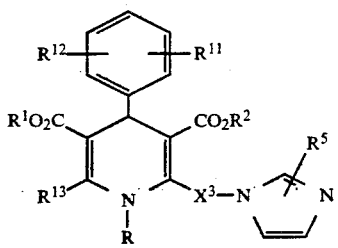

(Ia)

wherein R, $R^1$ and $R^2$ have the meanings given above, $R^5$ is H or lower alkyl, $X^3$ is $-CH_2-$, $-CH_2NHCH_2-$, $-CH_2NH(CH_2)_2-$, $-CH_2CH_2-$, $-(CH_2)_2O$, or $-CH_2O-$, $-CH(CH_3)-$; $R^{11}$ and $R^{12}$ are each selected from hydrogen, nitro, halo or trifluoromethyl, and $R^{13}$ is $NH_2$—or lower alkyl especially methyl; or a salt thereof, or an optically active isomer thereof.

In formula Ia preferably R is hydrogen.

Examples of $R^1$ are H, Me or Et. Examples of $R^2$ are Me and Et. When $R^{11}$ is hydrogen examples of $R^{12}$ are 3-nitro, 2-trifluoromethyl. Examples of $R^{11}$ and $R^{12}$ when substituents are 2,3-dihalo, e.g. are 2,3-dichloro, 3-nitro-2-halo and 3-halo-2-nitro. The term "lower" as used herein denotes 1 to 6 carbon atoms.

Other preferred compounds are compounds of formula Ia in which 1-imidazolyl is replaced by a pyridine ring, preferably pyrid-3-yl.

The compounds of formula I possess pharmaceutical activity in particular antihypertensive and/or hypotensive activity when tested on warm blooded animals and hence are indicated for the treatment of high blood pressure. In addition since the compounds of this invention antagonise calcium movement into the cell they are also vasodilators and useful in the treatment of a variety of cardiac conditions such as heart attacks, angina pectoris, cardiac arrythmias, cardiac hypertrophy and coronary vasospasm. Furthermore the compounds of formula I also inhibit blood platelet aggregation and inhibit thromboxane synthetase. These latter activities in combination with their antihypertensive properties makes these compounds potentially very useful for the treatment of cardiovascular disorders, especially thrombosis.

The compounds of formula I were tested for antihypertensive activity by the following standard procedure:

The blood pressures of male or female spontaneously hypertensive rats are measured in a 37° C constant temperature housing by means of a tail cuff. Rats with systolic pressures below 155 mmHg are discarded. Groups of rats are dosed orally with the test substance in a suitable vehicle or with vehicle alone. Systolic pressures are recorded before dosing and at selected time points afterwards. Heart rates are derived from caudal artery pulses. Results are analysed statistically by means of 2 way analysis of variance (within group).

In this procedure representative compounds of the invention gave the results shown in the following Table:

| COMPOUND | DOSE LEVEL (mmol/kg po) | BLOOD PRESSURE as % of pre-dose level (time t after dosing) | | |
|---|---|---|---|---|
| | | t = 2 hrs | 6 hrs | 24 hrs |
| 1,4-Dihydro-2-(imidazol- | 0.15 | 42% | 46% | 85 |
| 1-ylmethyl)-6-methyl-4-(3-nitrophenyl)pyridine-3,5-dicarboxylic acid 3-ethyl 5-methyl diester | 0.03 0.003 | 48% 65% | 62% 70% | 105% 83% |
| 1,4-Dihydro-2-[2-imidazol-1-yl)-ethyl]-6-methyl-4-(2-nitrophenyl)pyridine-3,5-dicarboxylic acid diethyl ester | 0.15 0.03 | 35% 63% | 42% 99% | 74% 105% |

Calcium antagonist activity was demonstrated by examining drug effect on the response of isolated rat portal vein to increasing calcium ion concentration in vitro. In this test a-molar concentration of $2 \times 10^{-7}$ M of 1,4-dihydro-2-(imidazol-1-ylmethyl)-6-methyl 4-(3-nitrophenyl)pyridine-3, 5-dicarboxylic acid 3-ethyl 5-methyl ester was required to reduce the response by 50%.

Compounds of formula I were tested for their ability to inhibit blood platelet aggregation by a modification of the procedure of Fantl, Australian J.Exp.Biol- Med.-Sci. 45, 355-62 1967.

Since platelet aggregation is the initial step in thrombus formation it is considered that compounds which prevent aggregation or reduce platelet adhesiveness may inhibit the initiation of the atherosclerotic process. The effect of drugs on adhesiveness is measured in platelet-rich plasma containing a small amount of arachidonic acid which markedly increases aggregation in vitro and may be a physiological agent for doing so in vivo. The actual test procedure used in described below.

New Zealand White rabbits (2.5-3kg) are anaesthetised with an injection, via the marginal ear vein, of sodium 30-40 mg/kg. The carotid artery is cannulated and blood (100-150 ml) is withdrawn into 50 ml syringes containing 3.8% sodium citrate (Ratio blood: citrate =9:1).

Blood is centrifuged at 200 g (1500 r.p.m.) for 10 minutes at 5° C. and the platelet rich plasma (PRP) removed. The platelets are then kept at room temperature in a screw topped plastic centrifuge tube for the duration of the experiment.

A twin channel platelet aggregometer—(HU aggregometer, A. Browne Ltd, Leicester, UK) is used. 1.0 ml aliquots of PRP are prewarmed for 5-10 minutes and stirred continuously at 1100 rpm. Aggregation is induced by addition of 250$\mu$M arachidonic acid, (8$\mu$l volume) to the PRP samples. The aggregometer output is set at maximum and the chart recorder sensitivity is altered to give a full scale deflection to this arachidonic acid response.

Control responses are recorded as the maximum deflection obtained after addition of 250$\mu$M arachidonic acid.

PRP samples are preincubated for 1 minute with the test compounds followed by arachidonic acid addition. The maximum deflection after the addition of arachidonic acid is then recorded. All drugs are screened initially at $10^{-4}$ M (final concentration), i.e. 10$\mu$l of a $1 \times 10^{-2}$M stock solution of the drug dissolved in distilled water is added to the PRP.

Dazoxiben, a thromboxane synthetase inhibitor (Randall, M. J. et al Research 23 145-162, 1981)is used as a positive control and all test components are compared with Dazoxiben. The activity of the test compound is expressed as the ratio $IC_{50}$ Dazaxiben/$IC_{50}$ Test where $IC_{50}$ is the dose required to inhibit the A.A. induced aggregation by 50%. The greater the ratio the more potent the compound relative to Dazoxiben.

| COMPOUND | Inhibition of blood platelet aggregation potency ratio (dazoxiben = 1) |
|---|---|
| 1,4-Dihydro-2-[2-(imidazol-1-yl)ethyl]-6-methyl-4-(2-nitrophenyl)pyridine-3,5-dicarboxylic acid diethyl ester | 0.79 |
| 1,4-Dihydro-2-(imidazol-1-ylmethyl)-6-methyl-4-(3-nitrophenyl)pyridine-3,5-dicarboxylic acid 3-ethyl 5-methyl diester | 1.2 |
| 1,4-Dihydro-2-[2-(imidazol-1-yl)-ethyl]-6-methyl-4-(2-nitrophenyl)-pyridine-3,5-dicarboxylic acid dimethyl ester | 1.64 |
| 1,4-Dihydro-2-methyl-4-(3-nitrophenyl)-6-[(3-pyridyloxy)methyl]pyridine-3,5-dicarboxylic acid 5-ethyl-3-methyl diester | 1.1 |

Compounds possessing thromboxane synthetase inhibitory activity are useful in the treatment or prevention of diseases responsive to the inhibition of thromboxane synthetase especially cardiovascular disorders such as thrombosis, artherosclerosis, cerebral ischaemic attacks; and angina pectoris; peripheral vascular diseases and migraine.

The compounds of formula I were tested for their ability to inhibit thromboxane production by the following standard test:

a) Generation of thromboxanes

Blood (approx. 75 ml) is obtained from an anaesthetised rabbit and centrifuged at 200 g for 10 minutes to obtain platelet rich plasma (PRP). An aliquot of PRP is incubated for 10 minutes at 37° C. in the presence of vehicle or drug. Platelet aggregation is induced by the addition of adenosine diphosphate and adrenalin. The tubes are incubated for 3 minutes, centrifuged at 10,000 for 3 minutes and a 50 ml aliquot of the supernatant taken for radio-immunoassay of thromboxane $B_2$ ($TxB_2$).

b) Radio-immunoassay of $TxB_2$

The total incubation volume is 150μ containing 50μl of $^3$H - $TxB_2$ (0.005 μCi), 50 ml of sample or authentic $TxB_2$ ranging from 5 to 300 pg per tube as standards and 50 μl of rabbit anti-sera to $TxB_2$ (in a concentration which will bind 50% of H-$TxB_2$) After incubation for 1 hour at room temperature the tubes are further incubated for 16-20 hours at 4° C. 1 ml of dextran-coated charcoal is then added to the tubes which are further incubated on ice for 10 minutes. Following the incubation the samples are centrifuged at 10,000 g for 10 minutes and 500 ml of the supernatant added to 5 ml of scintillation cocktail. Measurement of the radioactivity in the supernatant quantifies the amount of [$^3$H]-$TxB_2$ bound by the antibody. The concentration of unlabelled $TxB_2$ in the sample is then determined from a linear standard curve.

In the above mentioned test the representative compounds of Examples 1,2 and 5 gave $IC_{50}$ values of 5.0; 2.3 and 12.3 μM respectively In the same test the antihypertensive agent nifedipine had an $IC_{50} > 1000$μM. $IC_{50}$ values represent the concentrations of drug which achieve 50% inhibition of $TxB_2$.

Some compounds of formula I have also been found to possess Phospholipase $A_2$ ($PLA_2$) inhibitory activity and hence are also indicated for use as antiinflammatory and antiallergic agents. Of particular interest for this activity are compounds of formula I wherein Ar represents an aryl radical having a 2-nitro substituent. For example the compound of Example 2 produced a 77% inhibition of $PLA_2$ activity at a concentration of 100μM. $PLA_2$ activity was assayed by a procedure based on Franson, R.C., Chapter 12. Intracellular Metabolism of Ingested Phospholipids. Liposomes: from Physical Structure to Therapeutic Applications. North-Holland Biomedical Press, 1981, pp 349-380 and involving measuring the hydrolysis of E.coli membrane phospholipids and the release of free [1-$^{14}$C]oleic acid from the C-2 position of phospholipids by human platelet $PLA_2$.

This invention also provides processes for preparing the compounds of formula I. In general both the compounds of formula I and intermediates of analogous structure may be prepared by processes which are known or are analogous to known processes; see for example Drugs of the Future, Vol.VI, No. 7, 1981 pps 427-440. A first general process for preparing compounds of formula I as hereinbefore defined wherein B is hydrogen, lower alkoxycarbonyl, carboxyl, or optionally substituted lower alkyl with the provisos that a) r cannot be zero and
b) when Y is —S— or —NR$^8$—then p is 1 or 2, comprises reacting corresponding compounds of formula

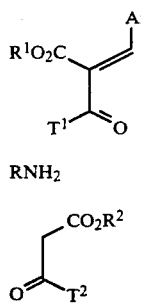

II

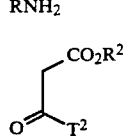

III

IV wherein Ar, R, R$^1$ and R$^2$ are as defined above, and one of T$^1$ and R$^2$ is A, the other is B wherein A and B are as defined immediately above. The process is conveniently carried out by heating, e.g. at reflux, in an inert solvent preferably polar such as ethanol, toluene, dimethylformamide, isopropranol, acetonitrile.

A second general process for preparing compounds of formula I as hereinbefore defined and subject to provisos a) and b) as in the first process mentioned above, comprises reacting a corresponding compound of formula II as shown above with a corresponding compound of formula

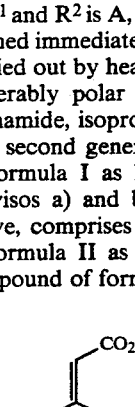

(V)

wherein Ar, R, $R^1$ and $R^2$ are as defined above, and one of $T^1$ and $T^2$ is A, the other is B providing that when $T^2$ is A then $T^1$ cannot be optionally substituted amino. This process may conveniently be carried out by heating e.g. at reflux in an inert solvent (preferably polar)- such as ethanol, acetonitrile, isopropranol, toluene or dimethylformamide.

In yet a further process compounds of formula I wherein provisos (a) and (b) above apply may be prepared by reacting a compound of formula ArCHO with corresponding compounds of formula VI and V shown below

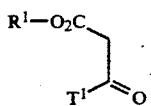

(VI)

and

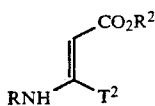

(V)

wherein Ar, R, $R^1$ and $R^2$ are as defined above and one of $T^1$ and $T^2$ is A, the other B, providing that when $T^2$ is A then $T^1$ cannot be optionally substituted amino. Such a process may be carried out by heating the reactants, e.g. at reflux, in an inert solvent(preferably polar) such as ethanol, acetonitrile, isopropranol, toluene or dimethylformamide.

Compounds of formula I may be prepared by reacting corresponding compounds of formula

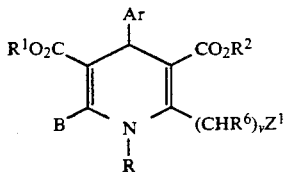

(VII)

and (VIII)

$Z^2(CHR^7)_wR^3$ in which formulae $B,R,R^1$, $R^2,R^3$, $R^6$ and $R^7$ are as defined above, one of $Z^1$ and $Z^2$ is halogen or a sulphonyloxy group; the other of $Z^1$ and $Z^2$ is -YH, $Y^-$, OH or $O^-$ as appropriate (wherein Y is as defined above) and v and w are each 0, 1 or 2 with the provisos that (i) when v is 2 and $Z^2$ is YH or $Y^-$ then $Z^1$ can also represent dialkylamino, e.g. $-NMe_2$ or a quaternary ammonium group, e.g. $-NMe_3^+$; and (ii) when one of $Z^1$ or $Z^2$ is OH or $O^-$ then one of v and w is O.

The reaction may be carried out in an inert solvent in the presence of base, e.g. $K_2C_2CO_3$ or a tertiary amine e.g. triethylamine. Anions of the requisite starting materials may be generated by the usual methods known in the art and reacted. Examples of sulphonyloxy are alkyl-or aralkyl-or arylsulphonyloxy,e.g. tosyloxy or mesyloxy.

The starting materials of formula VII wherein $Z^1$ is halogen, sulphonyloxy as defined above may be prepared by known methods, e.g. from corresponding compounds of formula

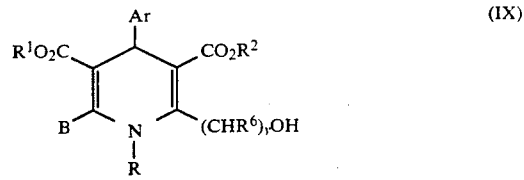

(IX)

by methods known for the conversion of OH to halogen or sulphonyloxy. Compounds of formula VIII wherein $v=O$ may be prepared by reacting a compound of formula X

(X)

wherein R, $R^1$ and B are as hereinbefore defined with compounds of formulae

(XI)

in which formula Ar and $R^2$ are as defined above.

Compounds of formula IX wherein v is 1 or 2 may be prepared by reacting a compound of formula

(XII)

wherein v is 1 or 2 and Ar and $R^2$ are as defined above with a compound of formula (X) as hereinbefore- defined.

Compounds of formula VII wherein v is 2 and $Z^1$ is $-N(alkyl)_2$ or a quaternary ammonium group may be prepared by performing a Mannich reaction on a compound of formula

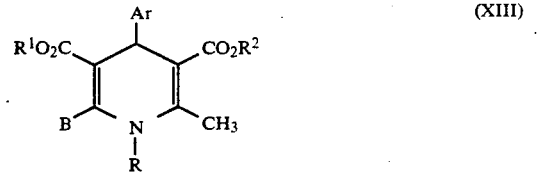

(XIII)

using formaldehyde and secondary amine and if required reacting the product with an alkyl halide. Compounds of formula VII wherein $Z^1$ is $Y^-$ or $O^-$ may be prepared by known methods. For example, when $Z^1$ is $-OH$, $-NHR^8$ or $-SH$ anions may be formed in the presence of a strong base, e.9. an alkali metal hydride such as NaH or BuLi. When Y is a direct bond carbanions may be prepared from the corresponding halo compound using for example, lithium diisopropylamine or BuLi.

In any of the aforementioned reactions reactive substituent groups may be protected if susceptible to the reaction conditions and deprotected afterwards.

Compounds of formula I wherein R is other than hydrogen may be prepared by alkylating a compound of formula I wherein R is H in the presence of a strong base, e.g. an alkali metal hydride, with a compound of formula R—halogen where R is as defined above other than hydrogen.

Compounds of formula I having ester functional groups, e.g. cyanoethyl- or t-butyl-ester, may be hydrolysed, selectively if appropriate, to give compounds of formula I having carboxyl groups. Alternatively carboxyl groups can be esterified.

The compounds of formula I possess one or more asymmetric centres and hence optical isomers and mixtures thereof are possible. All such isomers and mixtures thereof are included within the scope of this invention. Where any reaction process produces mixtures of such isomers standard resolution techniques may be applied to separate a specific isomer.

In any of the aforementioned reactions compounds of formula I may be isolated in free base form or as acid addition salts as desired. Examples of such salts include salts with pharmaceutically acceptable acids such as hydrochloric, hydrobromic, hydroiodic, sulphuric, phosphoric, nitric, acetic, citric, tartaric, fumaric, succinic, malonic, formic, maleic acid or organosulphonic acids such as methane sulphonic or p-tolyl sulphonic acids.

When acidic substituents are present it is also possible to form salts with bases e.g. alkali metal (such as sodium) or ammonium salts. Such salts of the compounds of formula I are included within the scope of this invention.

When basic substituents are present then quaternary ammonium salts may be formed by quaternizing with an alkylating agent such as alkyl, or alkyl halides.

Starting materials for the processes described herein are known compounds or can be prepared by analogous methods for known compounds.

This invention also provides pharmaceutical compositions comprising a compound of formula I or a pharmaceutically acceptable salt thereof.

For the pharmaceutical compositions any suitable carrier known in the art can be used. In such a composition, the carrier may be a solid, liquid or mixture of a solid and a liquid. Solid form compositions include powders, tablets and capsules. A solid carrier can be one or more substances which may also act as flavouring agents, lubricants, solubilisers, suspending agents, binders, or tablet disintegrating agents; it can also be encapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 5 to 99, preferably 10-80% of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax and cocoa butter. The term "composition" is intended to include the formulation of an active ingredient with encapsulating material as carrier, to give a capsule in which the active ingredient (with or without other carriers) is surrounded by carriers, which is thus in association with it. Similarly cachets are included.

Sterile liquid form compositions include sterile solutions, suspensions, emulsions, syrups and elixirs.

The active ingredient can be dissolved or suspended in a pharmaceutically acceptable carrier, such as sterile water, sterile organic solvent or a mixture of both. The active ingredient can often be dissolved in a suitable organic solvent, for instance aqueous propylene glycol containing from 10 to 75% of the glycol by weight is generally suitable. Other compositions can be made by dispersing the finely-divided active ingredient in aqueous starch or sodium carboxymethyl cellulose solution, or in a suitable oil, for instance arachis oil.

Preferably the pharmaceutical composition is in unit dosage form, the composition is sub-divided in unit doses containing appropriate quantities of the active ingredient; the unit dosage form can be a packaged composition, the package containing specific quantities of compositions, for example packeted powders or vials or ampoules. The unit dosage form can be a capsule, cachet or tablet itself, or it can be the appropriate number of any of these in packaged form. The quantity of active ingredient in a unit dose of composition may be varied or adjusted from 10 to 500 mg or more, e.g. 25 mg to 250 mg, according to the particular need and the activity of the active ingredient. The invention also includes the compounds in the absence of carrier where the compounds are in unit dosage form. Based on the results from animal studies the dosage range for the treatment of humans using a compound of formula I will be in the range from about 5 mg to 500 mg per day depending on the activity of the compound.

The following Examples illustrate the invention and methods for preparing compounds of the invention. Since the final product may be sensitive to light, light should be excluded whenever possible during and after synthesis of compounds of the invention.

EXAMPLE 1

1,4-Dihydro-2-(imidazol-1-ylmethyl)-6-methyl-4-(3-nitro-phenyl)pyridine-3,5-dicarboxylic acid 3-ethyl 5-methyl diester A mixture of methyl 2-(3-nitrobenzylidene)acetoacetate (2.5 g. 0.01 mol), ethyl 4-(imidazol-1-yl)acetoacetate 3 g,50% excess), ethanol (20 ml) and concentrated 0.880 ammonia (1 ml) was stirred for 1 hour and refluxed for 5 hours. The solvent was evaporated under reduced pressure and the residue chromatographed on alumina (Act I, neutral 120 g) using $CHCl_3$ initially as eluent to remove by-products and then 10% MeOH in $CHCl_3$ to elute the title compound.

Treatment of this in ethanol with ethanolic HCl gave the hydrochloride, hemihydrate salt of the title compound, m.p. 144°-146° C.

Analysis: $C_{21}H_{22}N_4O_6.HCl.\frac{1}{2}H_2O$ requires C, 53.45; N, 5.13; N, 11.87% Found: C, 53.46; H, 4.86; N, 11.67%.

EXAMPLE 2

1,4-Dihydro-2-[2-(imidazol-1-yl)-ethyl]-6-methyl-4-(2-nitrophenyl)pyridine-3,5-dicarboxylic acid diethyl ester a) A mixture of 1,4-dihydro-2,6-dimethyl-4-(2-nitrophenyl)pyridine-3,5-dicarboxylic acid diethyl ester (7.5 g, 0.02 mol), dimethylamine hydrochloride (2.44 g, 0.03 mol), paraformaldehyde (0.9 g, 0.03 mol), ethanol (35 ml) and 4 drops of concentrated HCl was heated at reflux for 10 hours. The solvent was then evaporated and the residue partitioned between dilute aqueous hydrochloric acid and ethyl acetate/diethyl ether. The aqueous acid phase was separated, basified with ammonia and back extracted into ether. The ether extract was dried and evaporated to give an oil. This was eluted down an alumina (250 g, Merck Act I) column using $CHCl_3$ as eluent to give 4 g. of 1,4-dihydro-6-methyl-2-(2-dimethylaminoethyl)-4-(2-nitrophenyl)-pyridine-3,5-dicarboxylic acid diethyl ester which crystallised on standing and was recrystallised from diisopropyl ether (10 ml) to give 1.8 g of crystalline compound.

b) A mixture of the product of step (a) above (2.15 g, 5mmol), imidazole (2.72 g, 40 mmol) and chlorobenzene (50ml) was heated at reflux for 3 days. The solution was then cooled, washed thrice with water, dried and evaporated. The residue was recrystallised from ethyl acetate to give the product 1.4 g (61.6%) m.p. 195°-8° C. The base was suspended in hot ethanol (5 ml) and maleic acid (0.375 g, 5% excess) added to give a clear solution. On cooling in ice the crystalline maleic acid salt of the title compound separated and was collected by filtration (1.55 g).

Recrystallisation from ethanol (6ml) gave 1.3 g mp. 140°-141° C.

Analysis:

$C_{23}H_{26}N_4O_6.C_4H_4O_4$ requires C, 56,84; H, 5.30; N, 9.82% Found: C, 57.10; H, 5.60; N, 9.50%.

EXAMPLE 3

1,4-Dihydro-2-[2-(1-imidazolyl)ethyl]-6-methyl-4-(2-nitrophenyl)pyridine-3,5-dicarboxylic acid dimethyl ester In a manner analogous to Example 2(b) with exclusion of light 1,4-dihydro-6-methyl-2-(2-(dimethylaminoethyl)-4-(2-nitrophenyl)pyridine-3,5-dicarboxylic acid dimethyl ester (1.61 g), 4 mmol) was reacted with imidazole (2.17 g, 32 mmol) in the presence of chlorobenzene (40 ml) to give the title compound (0.39 g).

This was suspended in warm isopropyl alcohol (4 ml), maleic acid (0.113 g, 1.05 equiv.) was added and the mixture stirred at room temperature for 2 hours to give 0.46 g of the maleic acid salt, mp 176°-7° C.

Analysis: $C_{21}H_{22}N_4O_6.C_4H_4O_4$ requires (55.35; H, 4.83; N, 10.33% Found: C, 55.71; H, 5.02; N, 10.03%.

EXAMPLE 4

1,4-Dihydro-2methyl-4-(3-nitrophenyl)-6-[(3-pyridyloxy) methyl]pyridine-3,5-dicarboxylic acid 5-ethyl-3-methyl diester Ethyl 2-(3-nitrobenzylidene)acetoacetate (6.47 g. 0.026mol), ethyl 3-oxo-4-(3-pyridyloxy)butanoate (5.8 g, 0.026 mol) and 0.88 ammonia (2.5 ml) in ethanol were refluxed for 7 hours. The solvent was removed under reduced pressure and the residue partitioned between 2N hydrochloric acid and diethyl ether. The aqueous acid was extracted with chloroform and this was washed with dilute ammonia solution, dried ($MgSO_4$) and evaporated. The residue was purified by chromatography on silica with chloroform as eluent to give as a first major product the title compound. This was dissolved in ethyl acetate and treated with ethanolic HCl. Evaporation to low volume followed by addition of diethyl ether gave the hydrochloride salt of the title compound (4.15 g). mp. 201°-203° C.

Analysis:

$C_{23}H_{23}N_3O_7.HCl$ requires C, 56.39; H, 4.94; N, 8.58% Found: C, 56.53; H, 5.22; N, 8.91%.

EXAMPLE 5

2-[2-(1-Benzimidazolyl)ethyl]-4-[2,3-dichlorophenyl]-1,4-dihydro-6-methylpyridine-3,5-dicarboxylic acid dimethylester A mixture of 4-(2,3-dichlorophenyl)-1,4-dihydro-6-methyl-2-(2-(dimethylaminoethyl)pyridine 3,5-dicarboxylic acid dimethyl ester (2.14 g, 5 mmol), benzimidazole (2.36 g, 20 mmol)1,8-diazabicyclo[5.4.0]undec-7-ene (0.75 g, 5 mmol) and chlorobenzene (50 ml was heated at reflux for 24 hours. The solution was then diluted with chloroform (50 ml) washed with water dried and evaporated. The residue was triturated 3 times with warm toluene to give the title compound 1.5 g. This was suspended in methyl acetate (25 ml) and acidified with ethanolic HCl to precipitate the hydrochloride (1.5 g.) which was recrystallised from 1:1 aqueous methanol mp 155°-158° C.

Analysis:

$C_{25}H_{23}Cl_2N_3O_4.HCl.\frac{1}{2}H_2O$ requires: C,55.01; H,4.62; N, 7.70% Found: 2,54.96; H, 4.46, N, 7.50%.

EXAMPLE 6

4-(2,3-Dichlorophenyl)-1,4-dihydro-2-methyl-6-(2-[2-methyl(1-imidazolyl)]ethyl)pyridine-3,5-dicarboxylic acid, dimethyl ester.

A mixture of 4-(2,3-dichlorophenyl)-1,4-dihydro-6-methyl-2-(2-dimethylaminoethyl)pyridine 3,5-dicarboxylic acid dimethyl ester (2.14 g, 5mmol), 2-methylimidazole (1.64 g, 20mmol), 1,8-diazabicyclo[5.4.0]undec-7-ene (0.75 g, 5mmol) and chlorobenzene (50ml) was heated at reflux for 24hours. The solution was cooled, diluted with chloroform (25ml), washed with water (100ml), dried and evaporated. The residue was chromatographed on silica gel (50 g, Act I) using chloroform-methanol as eluent to give the title compound. This was suspended in methanol (10ml) and acidified by addition of maleic acid (0.5 g, 5% excess) to give a clear solution which was then diluted with ether (10ml) to precipitate the crystalline maleate salt 1.65 g mp 197°-198°.

Analysis $C_{22}H_{23}Cl_2N_3O_4.C_4H_4O_4$ requires: C, 53.80, H, 4.69; N,7.24% Found: C, 54.15, H, 4.75, N, 6.97%.

EXAMPLE 7

4-(2,3-Dichlorophenyl)-1,4-dihydro-2-[2-(1-imidazolyl)-ethyl]-6-methylpyridine-3,5-dicarboxylic acid, dimethyl ester In a manner analogous to Example 6 but using imidazole instead of 2-methylimidazole the title compound was prepared as the maleate salt, mp 180°-182° C.

Analysis $C_{21}H_{21}N_3Cl_2O_4.C_4H_4O_4$ requires C, 53.01; H, 4.45; N, 7.42% Found: C, 52.99; H 4.37; N, 7.66%.

EXAMPLE 8

1,4-Dihydro-2-[2-(1-imidazolyl)ethyl]-6-methyl-4-(3-nitrophenyl)pyridine-3,5-dicarboxylic acid diethyl ester 1,4-Dihydro-6-methyl-2-(2-dimethylaminoethyl)-4-(3-nitrophenyl)pyridine-3,5-dicarboxylic acid diethyl ester (1.72 g, 4mmol, prepared by analogy with Example 2(a)), methyl iodide (1ml) and methanol (20ml) were refluxed for 1 hour, then evaporated to give a glass. This was dissolved in chlorbenzene (20ml) and imidazole (2.17 g, 32 mmol) was added. The mixture was refluxed for 13 hours and cooled to room temperature overnight, then washed three times with water, dried and evaporated to give a solid, 0.68 g. The sample was suspended in boiling methanol (5 ml) and ethanolic HCl was added to give an acidic solution. This was cooled in ice and diluted with ether (15ml). The resulting precipitate was triturated in ice, collected and dried (0.82) to give the title compound as the HCl, $\frac{1}{4}H_2O$ salt, mp 174°–5° C.

Analysis $C_{23}H_{26}N_4O_6 \cdot HCl \cdot \frac{1}{4}H_2O$ requires: C,55.76; H, 5.60; N, 11.31% Found: C, 55.96; H, 5.50; N, 10.98%.

EXAMPLE 9

1,4-Dihydro-2-(1-imidazolylmethyl)-6-methyl-4-(3-nitrophenyl)pyridine-3,5-dicarboxylic acid diethyl ester 3-Nitrobenzaldehyde (1.51 g, 10mmol), ethyl 3-aminocrotonate (1.34 g, 10mmol), and ethyl 3-oxo-4-(1-imidazolyl)butanoate oxalate. (2.86 g, 10mmol) were heated together in absolute ethanol (50 ml) for 30 minutes under nitrogen. 0.880 ammonia (3 ml, 43.5 mmol) was added to the hot suspension, giving, after a further 1 hour at reflux, a clear solution which then deposited a solid. After 5 hours at reflux the mixture was allowed to cool overnight under $N_2$ with exclusion of light.

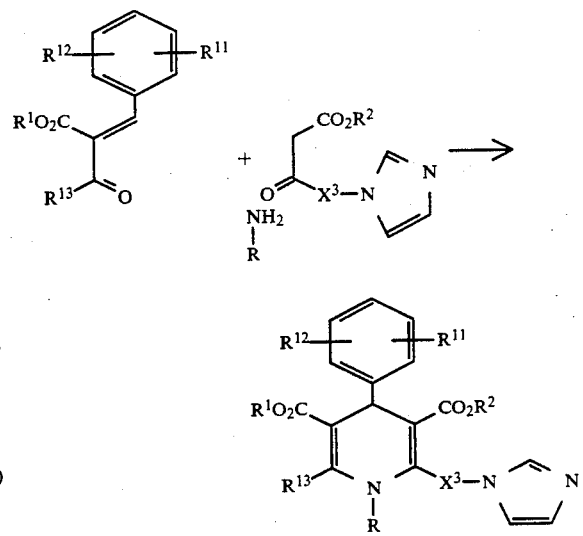

the following compounds of formula Ia are prepared:

| Ex No. | R | $R^1$ | $R^2$ | $R^{11/12}$ | $R^{13}$ | $-X^3-$ | m.p.(°C.) |
|---|---|---|---|---|---|---|---|
| 10 | H | $-(CH_2)_2CN$ | Et | H,2-$NO_2$ | Me | $-CH_2$ | |
| 11 | H | $^tBu$ | Et | H,3-$NO_2$ | Me | $-CH_2$ | 150–156 (HCl hemihydrate) |
| 12 | H | Me | Et | H,2-Cl | Me | $-CH_2-$ | 190° C. |
| 13 | H | $^iPr$ | Et | H,3-$NO_2$ | Me | $-CH_2-$ | 115–117° (HCl, ethanolate salt) |
| 14 | H | Me | Et | 2,3-diCl | Me | $-CH_2-$ | |
| 15 | H | Et | Et | H,3-$NO_2$ | $EtO_2C-$ | $-CH_2-$ | |
| 16 | H | Me | Et | H,3-$NO_2$ | $EtO_2CCH_2-$ | $-CH_2-$ | |

The precipitate was removed and discarded, and filtrate was evaporated to give an oil, which was partitioned between ether (25ml) and 2N hydrochloric acid (10ml). The acid phase was extracted with further ether (2×15 ml), and the combined ether phases were washed with water (10 ml) and discarded. The acid phase and the water wash were combined and extracted with chloroform (3×20 ml). The $CHCl_3$ extracts were combined, dried ($Na_2SO_4$) and evaporated to give a foam (1.99 g). This was crystallised from ethyl acetate (30 ml) to give the title compound (1.2 g) mp 137°–140°. This material was treated with ethanolic HCl and recrystallised from ethyl acetate-ethanol to give the $HCl \cdot H_2O$ salt (0.84 g, mp 132°–7°.

Analysis $C_{22}H_{24}N_4O_6 \cdot HCl \cdot H_2O$ requires C, 53.4; H, 5.5; N, 11.3% Found: C, 53.8; H, 5.4; N, 11.1

EXAMPLES 10–14

By the general procedure described in Example 1 using reactants according to the following reaction scheme

EXAMPLE 17–20

The compounds of Examples 10 and 11 are hydrolysed under basic conditions (using aqueous 1,2-dimethoxymethane) or acidic conditions respectively to give Example 17: 1,4-dihydro-2-(imidazol-1-ylemthyl)-6-methyl-4-(2-nitrophenyl)pyridine-3,5-dicarboxylic acid 3-ethyl ester.

Example 18: 1,4-dihydro-2-(imidazo-1-ylmethyl)-6-methyl-4-(3-nitrophenyl)pyridine-3,5-dicarboxylic acid 3-ethyl ester.

The compounds of Example 15 and 16 are hydrolysed under basic conditions to give respectively:

Example 19: 1,4-dihydro-2-(1-imidazolylmethyl)-4-(3-nitrophenyl)pyridine -3,5,6-tricarboxylic acid 3,5-diethyl ester.

Example 20: 1,4-dihydro-3-carbethoxy-5-carbomethoxy-2-(1-imidazolylmethyl)-4-(3-nitrophenyl)-pyridine-6-acetic acid.

EXAMPLE 21

The compound of Example 1 is treated with sodium hydride and ethyl chloroacetate to give: 1,4-dihydro-1-carbethoxymethyl-2-(imidazol-1-ylmethyl)-6-methyl-4-(3-nitrophenyl)pyridine, 3,5-dicarboxylic 3-ethyl 5-methyl ester

EXAMPLES 22–32

Using a procedure analogous to Example 9 and according to the reaction scheme.

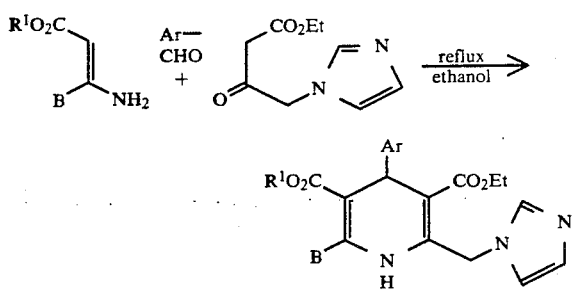

the following compounds of formula I are prepared

| Ex. No. | Ar | R¹ | B | m.p. °C. |
|---|---|---|---|---|
| 22. | 3-nitrophenyl | Et | NH₂ | 174-5 (maleate) |
| 23. | pentafluorophenyl | Me | Me | 200-208 (HCl) |
| 24. | 2-trifluoromethylphenyl | Me | Me | 165-8 (succinate) |
| 25. | 3-methylthien-2-yl | Me | Me | 155-159 (succinate) |
| 26. | quinol-4-yl | Me | Me | 153-156 (diHCl, H₂O salt) |
| 27. | benzofurazan-4-yl | Me | Me | 186.5-190 (HCl) |
| 28. | 3-nitrophenyl | 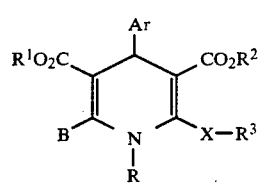 | Me | |
| 29. | naphth-1-yl | Me | Me | |
| 30 | 2-(difluoromethoxy)phenyl | Me | Me | |
| 31 | 3-cyanophenyl | Me | Me | |
| 32 | 2-methoxyphenyl | Me | Me | |

EXAMPLE 33

1,4-Dihydro-2-(imidazol-1-ylmethyl)-6-methyl-4-(3-nitro-phenyl)pyridine-3,5-dicarboxylic acid 3-(2-methoxy)ethyl 5-methyl ester A mixture of methyl 2-(3-nitrobenzylidene)-acetoacetate (2.5 g, 0.01 mol), ethanol (20 ml) and 2-methoxyethyl 3-amino-4-(imidazol-1-yl)crotonate (3 g) is heated at reflux for 5 hours to give the title compound.

EXAMPLE 34

4-(2,3-Dichlorophenyl)-1,4-dihydro-2-(1-imidazolylmethyl)-6-methylpyridine-3,5-dicarboxylic acid, dimethyl ester Pyridinium perbromide hydrobromide (5.6 g, 17.5 mmol) was added to a stirred ice-cooled solution of 4-(2,3-dichlorophenyl)-1,4-dihydro-2,6-dimethylpyridine-3,5-dicarboxylic acid dimethylester (5.55 g, 15 mmol) and pyridine (2 g) in methylene dichloride (80ml). The solution was stirred at ice temperature for 40 minutes then washed with ice cold water ( 1×100 ml). The organic phase was separated and imidazole (6.8 g, 0.1 mol) added followed by anhydrous Na₂SO₄. After drying for 20 minutes the solution was filtered to remove NaSO₄, evaporated and the residue heated on a steam bath for 40 minutes. The residue was then dissolved in EtOAc, washed with water (2×50 ml), dried, evaporated and crystallised from methyl acetate (15 ml) to give the crystalline title compound (3.34 g). This was suspended in isopropyl alcohol/methyl acetate (2:3 v/v)and acidified with ethanolic HCl to give the hydrochloride salt on cooling, m.p. 167°-170° C.

Analysis:

C₂₀H₁₉N₃Cl₂O₄.HCl 0.5 H₂O requires: C,49.86; H, 4.39;N,8.72%

Found: C, 49.98; H, 4.34; N, 8.54%.

EXAMPLE 35

1,4-Dihydro-2-(1-imidazolylmethyl)-6-methyl-4-(3-nitro-phenyl)pyridine-3,5-dicarboxylic acid dimethyl ester In a manner analogous to Example 34 1,4-dihydro-2,6-dimethyl-4-(3-nitrophenyl)pyridine-3,5-dicarboxylic acid 3,5 dimethyl ester was reacted with pyridinium perbromide hydrobromide and then imidazole to give the title compound, m.p. 223°-224° C. (hydrochloride salt).

Analysis:

C₂₀H₂₀H₄O₆.HCl requires: C,53.51;H,4.72;N,12.48%
Found: C, 53.66; H, 4.95; N, 12.48%.

We claim:

1. A compound of the formula $$\underset{B}{\overset{R^1O_2C}{\longrightarrow}}\underset{\underset{R}{N}}{\overset{Ar}{\longrightarrow}}\underset{X-R^3}{\overset{CO_2R^2}{\longrightarrow}}$$

or a pharmaceutically acceptable salt thereof, wherein
Ar is an aryl or heteroaryl radical of 5 to 10 ring atoms, the heteroaryl radical having 1 or 2 heteroatoms selected from N, O and S, which is optionally substituted by one or more substituents selected from halogen, alkyl, alkoxy, haloalkyl, haloalkoxy, NO₂, NH₂, CN, alkylamino, dialkylamino, aminoalkyl, carboxyl, alkoxycarbonyl, loweralkanoyl, loweralkanoylamino, and aryl of 5 to 10 ring atoms;
R represents hydrogen or an alkyl group or an arylkyl group wherein aryl of aralkyl is an aryl or an heteroaryl radical of 5 to 10 ring atoms, the heteroaryl radical having 1 or 2 heteroatoms selected from N, O and S, which is optionally substituted as above for aryl or heteroaryl of Ar;
R¹ and R² are the same or different and are selected from hydrogen and saturated C₅-C₇ cyclic aliphatic hydrocarbon residues, unsaturated acyclic aliphatic hydrocarbon residues of up to 6 carbon atoms and saturated $C_1$-$C_6$ acyclic hydrocarbon residues, said residues being optionally substituted by one or more groups selected from halogen, OH, carboxy, CN, alkoxy, alkylthio, aryloxy, alkoxycarbonyl, amino, mono- or diloweralkylamino, and an aryl or heteroaryl radical of 5 to 10 ring atoms the heteroaryl radical having 1 or 2 heteroatoms selected from N, O and S;

X is $Z^1$, $-Z^1(CH_2)_n-$, $-(CH_2)_n-$, $-(CH_2)_nZ^1-$, $-(CH_{2n}-$, $-CHR^6CH_2-$, $-CH_2CHR^7-$, or $-CHR^6CHR^7-$, wherein n is 1 or 2, $Z^1$ is $NR^8$, O or S, $R^6$ and $R^7$ each represent a lower alkyl group, and $R^8$ represents hydrogen or a lower alkyl group;

$R^3$ is mono- or bicyclic nitrogen ring heteroaryl radical containing 5 to 10 ring atoms of which 1 or 2 are optionally further heteroatoms selected from O, N and S, said radical optionally substituted by 1 to 3 substituents selected from halogen, alkyl, alkoxy, haloalkyl, haloalkoxy, $NO_2$, $NH_2$, CN, alkylamino, dialkylamino, aminoalkyl, carboxy, alkyloxycarbonyl, loweralkanoyl, loweralkanoylamino, phenyl, and heteroaryl of 5 to 10 ring atoms and 1 or 2 heteroatoms selected from N, O, and S; and B represents hydrogen, carboxyl, lower alkoxycarbonyl, lower alkyl, aminoloweralkyl, lower alkoxyloweralkyl, lower alkoxycarbonylloweralkyl, carboxyloweralkyl, amino, mono-loweralkylamino or di-loweralkylamino, wherein alkyl, alone or in combination, refers to $C_1$-$C_6$ alkyl.

2. A compound as claimed in claim 1 in which $R^3$ represents a mono- or bicyclic nitrogen ring heteroaryl radical containing 5 to 10 ring atoms of which 1 to 3 are nitrogen ring atoms.

3. A compound as claimed in claim 1 in which $R^3$ imidazolyl, pyridyl, thiazolyl, pyrrolyl, benzimidazolyl, quinolyl, isoquinolyl or imidazopyridyl.

4. A compound as claimed in claim 1 wherein Ar is phenyl, pyridyl, quinolyl or benzimidazolyl optionally substituted as for Ar in claim 1.

5. A compound as claimed in claim 1 wherein Ar is 2- or 3-nitrophenyl, 2,3-dichlorophenyl, 2-trifluoromethylphenyl, pentafluoromethyl, pentafluorophenyl, naphthyl, pyridyl or halopyridyl.

6. A compound as claimed in claim 1 wherein B is H, $CH_3-$, $NH_2-$, $NMe_2-$, $NHMe-$, $NH_2CH_2-$, $CH_3CH_2-$, $CH_3OCH_2-$, $CH_3OOC-$, $CH_3OOCCH_2-$, HOOC or $HOOCCH_2-$.

7. A compound as claimed in claim 1 wherein R is hydrogen, methyl, ethyl, n-propyl, isopropyl, benzyl, carbethoxymethyl or carbmethoxymethyl.

8. A compound as claimed in claim 1 wherein $R^1$ and/or $R^2$ represent hydrogen or saturated or unsaturated acrylic hydrocarbon chains of up to 6 carbon atoms optionally substituted by aryl having 5 to 10 ring atoms, lower alkoxy, amino, diloweralkylamino, carboxy or loweralkoxycarbonyl.

9. A compound as claimed in claim 1 wherein $R^1$ and $R^2$, independently, represent hydrogen, methyl, ethyl, n-propyl, isopropyl, butyl, methoxymethyl, ethoxymethyl, methoxypropyl, aminomethyl, 2-aminoethyl, 3-aminopropyl, dimethylaminoethyl, 2-carboxyethyl, methoxycarbonylmethyl, ethoxycarbonylmethyl, pyridylmethyl, pyridylethyl, imidazolylmethyl or imidazolylethyl.

10. A compound as claimed in claim 1 which is 1,4-dihydro-2-(imidazol-1-ylmethyl)-6-methyl-4-(3-nitrophenyl)pyridine-3,5-dicarboxylic acid 3-ethyl 5-methyl diester or a pharmaceutically acceptable salt thereof.

11. A compound as claimed in claim 1 which is 1,4-dihydro-2-[2-(imidazol-1-yl)-ethyl]-6-methyl-4-(2-nitrophenyl)pyridine-3,5-dicarboxylic acid diethyl ester or a pharmaceutically acceptable salt thereof.

12. A compound as claimed in claim 1 which is 1,4-dihydro-2-[2-(1-imidazolyl)ethyl]-6-methyl-4-(2-nitrophenyl)pyridine-3,5-dicarboxylic acid dimethyl ester or a pharmaceutically acceptable salt thereof.

13. A compound as claimed in claim 1 which is 1,4-dihydro-2-methyl-4-(3-nitrophenyl)-6-[(3-pyridyloxy)-methyl]pyridine-3,5-dicarboxylic acid 5-ethyl-3-methyl diester or a pharmaceutically acceptable salt thereof.

14. A compound as claimed in claim 1 which is 2-[2-(1-benzimidazolyl)ethyl]-4-[2,3-dichlorophenyl]-1,4-dihydro-6-methylpyridine-3,5-dicarboxylic acid dimethylester or a pharmaceutically acceptable salt thereof.

15. A compound as claimed in claim 1 which is 4-(2,3-dichlorophenyl)-1,4-dihydro-2-methyl-6-(2-[2-methyl(1-imidazolyl)]ethyl)pyridine-3,5-dicarboxylic acid, dimethyl ester or a pharmaceutically acceptable salt thereof.

16. A compound as claimed in claim 1 which is 4-(2,3-dichlorophenyl)-1,4-dihydro-2-[2-(1-imidazolyl-ethyl]-6-methylpyridine-3,5-dicarboxylic acid, dimethyl ester or a pharmaceutically acceptable salt thereof.

17. A compound as claimed in claim 1 which is 1,4-dihydro-2-[2-(1-imidazolyl)]ethyl-6-methyl-4-(3-nitrophenyl)pyridine-3,5-dicarboxylic acid diethyl ester or a pharmaceutically acceptable salt thereof.

18. A compound as claimed in claim 1 which is 1,4-dihydro-2-(1-imidazolylmethyl)-6-methyl-4-(3-nitrophenyl)pyridine-3,5-dicarboxylic acid diethyl ester or a pharmaceutically acceptable salt thereof.

19. A compound as claimed in claim 1 which is 1,4-dihydro-2-(imidazolyl-1-ylmethyl)-6-methyl-4-(3-nitrophenyl)pyridine-3,5-dicarboxylic acid 3-ethyl 5-isopropyl diester or a pharmaceutically acceptable salt thereof.

20. A compound as claimed in claim 1 which is 1,4-dihydro-2-(imidazo-1-ylmethyl)-6-methyl -4-(quinol-4-yl)pyridine-3,5-dicarboxylic acid 3-ethyl 5-methyl diester or a pharmaceutically acceptbale salt thereof.

21. A pharmaceutical composition comprising an amount of a compound of claim 1, or a pharmaceutically acceptable salt thereof, effective to lower blood pressure and a pharmaceutically acceptable carrier.

22. A pharmaceutical composition comprising an amount of a compound of claim 1, or a pharmaceutically acceptable salt thereof, effective to alleviate cardiac conditions susceptible to treatment by vasodilation and a pharmaceutically acceptable carrier.

23. A method of inhibiting blood platelet aggregation in a mammal, including man, in need thereof, comprising administering to such mammal an amount effective to inhibit blood platelet aggregation of a compound of the formula:

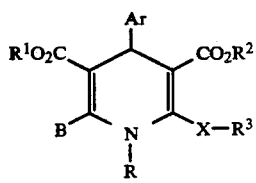

or a pharmaceutically acceptable salt thereof, wherein

Ar is an aryl or heteroaryl radical of 5 to 10 ring atoms, the heteroaryl radical having 1 or 2 heteroatoms selected from N, O and S, which is optionally substituted by one or more substituents selected from halogen, alkyl, alkoxy, haloalkyl, haloalkoxy, $NO_2$, $NH_2$, CN, alkylamino, dialkylamino, aminoalkyl, carboxy, alkoxycarbonyl, loweralkanoyl, loweralkanoylamino, and aryl of 5 to 10 ring atoms;

R represents hydrogen or an alkyl group or an aralkyl group wherein aryl of aralkyl is an aryl or an heteroaryl radical of 5 to 10 ring atoms, the heteroaryl radical having 1 or 2 heteroatoms selected from N, O and S, which is optionally substituted as above for aryl or heteroaryl of Ar;

$R^1$ and $R^2$ are the same or different and are selected from hydrogen and saturated $C_5$-$C_7$ cyclic aliphatic hydrocarbon residues, unsaturated acyclic aliphatic hydrocarbon residues of up to 6 carbon atoms and saturated $C_1$-$C_6$ acyclic hydrocarbon residues, said residues being optionally substituted by one or more groups selected from halogen, OH, carboxy, CN, alkoxy, alkylthio, aryloxy, alkoxycarbonyl, amino, mono- or diloweralkylamino, and an aryl or heteroaryl radical of 5 to 10 ring atoms the heteroaryl radical having 1 to 2 heteroatoms selected from N, O and S;

X is $Z^1$, —$Z^1(CH_2)_n$—, —$(CH_2)_nZ^1$—, —$(CH_2)_n$—, —$CHR^6CH_2$—, —$CH_2CHR^7$—, or —$CHR^6CH$-$R^7$—, wherein n is 1 or 2, $Z^1$ is $NR^8$, O or S, $R^6$ and $R^7$ each represent a lower alkyl group, and $R^8$ represents hydrogen or a lower alkyl group;

$R^3$ is mono- or bicyclic nitrogen ring heteroaryl radical containing 5 to 10 ring atoms of which 1 or 2 are optionally further heteroatoms selected from O, N and S, said radical optionally substituted by 1 to 3 substituents selected from halogen, alkyl, alkoxy, haloalkyl, haloalkoxy, $NO_2$, $NH_2$, CN, alkylamino, dialkylamino, aminoalkyl, carboxy, alkyloxycarbonyl, loweralkanoyl, loweralkanoylamino, phenyl, and heteroaryl of 5 to 10 ring atoms and 1 or 2 heteroatoms selected from N, O, and S; and B represents hydrogen, carboxyl, lower alkoxycarbonyl, lower alkyl, aminoloweralkyl, lower alkoxyloweralkyl, lower alkoxycarbonylloweralkyl, carboxyloweralkyl, amino, mono-loweralkylamino or di-loweralkylamino, wherein alkyl, alone or in combination, refers to $C_1$-$C_6$ alkyl.

24. A method of inhibiting thromboxane synthetase in a mammal, including man, in need thereof, comprising administering to such mammal an amount effective to inhibit thromboxane synthetase of a compound of the formula:

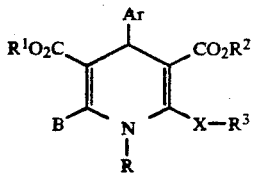

or a pharmaceutically acceptable salt thereof, wherein
Ar is an aryl or heteroaryl radical of 5 to 10 ring atoms, the heteroaryl radical having 1 or 2 heteroatoms selected from N, O and S, which is optionally substituted by one or more substituents selected from halogen, alkyl, alkoxy, haloalkyl, haloalkoxy, $NO_2$, $NH_2$, CN, alkylamino, dialkylamino, aminoalkyl, carboxy, alkoxycarbonyl, loweralkanoyl, loweralkanoylamino, and aryl of 5 to 10 ring atoms;

R represents hydrogen or an alkyl group or an arylkyl group wherein aryl of aralkyl is an aryl or an heteroaryl radical of 5 to 10 ring atoms, the heteroaryl radical having 1 or 2 heteroatoms selected from N, O and S, which is optionally substituted as above for aryl or heteroaryl of Ar;

$R^1$ and $R^2$ are the same or different and are selected from hydrogen and saturated $C_5$-$C_7$ cyclic aliphatic hydrocarbon residues, unsaturated acyclic aliphatic hydrocarbon residues of up to 6 carbon atoms and saturated $C_1$-$C_6$ acyclic hydrocarbon residues, said residues being optionally substituted by one or more groups selected from halogen, OH, carboxy, CN, alkoxy, alkylthio, aryloxy, alkoxycarbonyl, amino, mono- or diloweralkylamino, and an aryl or heteroaryl radical of 5 to 10 ring atoms the heteroaryl radical having 1 to 2 heteroatoms selected from N, O and S;

X is $Z^1$, —$Z^1(CH_2)_n$—, —$(CH_2)_nZ^1$—, —$(CH_2)_n$—, —$CHR^6CH_2$—, —$CH_2CHR^7$—, or —$CHR^6CH$-$R^7$—, wherein n is 1 or 2, $Z^1$ is $NR^8$, O or S, $R^6$ and $R^7$ each represent a lower alkyl group, and $R^8$ represents hydrogen or a lower alkyl group;

$R^3$ is mono- or bicyclic nitrogen ring heteroaryl radical containing 5 to 10 ring atoms of which 1 or 2 are optionally further heteroatoms selected from O, N and S, said radical optionally substituted by 1 to 3 substituents selected from halogen, alkyl, alkoxy, haloalkyl, haloalkoxy, $NO_2$, $NH_2$, CN, alkylamino, dialkylamino, aminoalkyl, carboxy, alkyloxycarbonyl, loweralkanoyl, loweralkanoylamino, phenyl, and heteroaryl of 5 to 10 ring atoms and 1 or 2 heteroatoms selected from N, O, and S; and B represents hydrogen, carboxyl, lower alkoxycarbonyl, lower alkyl, aminoloweralkyl, lower alkoxyloweralkyl, lower alkoxycarbonylloweralkyl, carboxyloweralkyl, amino, mono-loweralkylamino or di-loweralkylamino, wherein alkyl, alone or in combination, refers to $C_1$-$C_6$ alkyl.

25. A method of inhibiting phospholipase $A_2$ ($PLA_2$) in a mammal, including man, in need thereof comprising administering to such mammal an amount effective to inhibit phospholipase $A_2$ ($PLA_2$) of a compound of the formula:

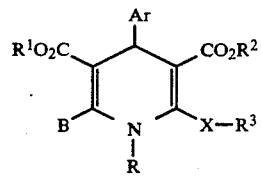

or a pharmaceutically acceptable salt thereof, wherein
Ar is an aryl or heteroaryl radical of 5 to 10 ring atoms, the heteroaryl radical having 1 or 2 heteroatoms selected from N, O and S, which is optionally substituted by one or more substituents selected from halogen, alkyl, alkoxy, haloalkyl, haloalkoxy, $NO_2$, $NH_2CN$, alkylamino, dialkylamino, aminoalkyl, carboxy, alkoxycarbonyl, loweralkanoyl, lowralkanoylamino, and aryl of 5 to 10 ring atoms;

R represents hydrogen or an alkyl group or an aralkyl group wherein aryl of aralkyl is an aryl or an heteroaryl radical of 5 to 10 ring atoms, the heteroaryl radical having 1 or 2 heteroatoms selected from N, O and S, which is optionally substituted as above for aryl or heteroaryl of Ar;

$R^1$ and $R^2$ are the same or different and are selected from hydrogen and saturated $C_5$-$C_7$ cyclic aliphatic hydrocarbon residues, unsaturated acyclic aliphatic hydrocarbon residues of up to 6 carbon atoms and saturated $C_1$-$C_6$ acyclic hydrocarbon residues, said residues being optionally substituted by one or more groups selected from halogen, OH, carboxy, CN, alkoxy, alkylthio, aryloxy, alkoxycarbonyl, amino, mono- or diloweralkylamino, and an aryl or heteroaryl radical of 5 to 10 ring atoms the heteroaryl radical having 1 or 2 heteroatoms selected from N, O and S;

X is $Z^1$, $-Z^1(CH_2)_n-$, $-(CH_2)_nZ^1-$, $-(CH_2)_n-$, $-CHR^6CH_2-$, $-CH_2CHR^7-$, or $-CHR^6CHR^7-$, wherein n is 1 or 2, $Z^1$ is $NR^8$, O or S, $R^6$ and $R^7$ each represent a lower alkyl group, and $R^8$ represents hydrogen or a lower alkyl group;

$R^3$ is mono- or bicyclic nitrogen ring heteroaryl radical containing 5 to 10 ring atoms of which 1 or 2 are optionally further heteroatoms selected from O, N and S, said radical optionally substituted by 1 to 3 substituents selected from halogen, alkyl, alkoxy, haloalkyl, haloalkoxy, $NO_2NH_2$, CN, alkylamino, dialkylamino, aminoalkyl, carboxy, alkyloxycarbonyl, loweralkanoyl, loweralkanoylamino, phenyl, and heteroaryl of 5 to 10 ring atoms and 1 or 2 heteroatoms selected from N, O, and S; and B represents hydrogen, carboxyl, lower alkoxycarbonyl, lower alkyl, aminoloweralkyl, lower alkoxyloweralkyl, lower alkoxycarbonylloweralkyl, carboxyloweralkyl, amino, mono-loweralkylamino or di-loweralkylamino, wherein alkyl, alone or in combination, refers to $C_1$-$C_6$ alkyl.

* * * * *